United States Patent [19]

Modak et al.

[11] Patent Number: 5,708,023
[45] Date of Patent: Jan. 13, 1998

[54] ZINC GLUCONATE GEL COMPOSITIONS

[75] Inventors: Shanta M. Modak, Riveredge, N.J.; Lester A. Sampath, Nyack, N.Y.; Balram H. Advani, Upper Saddle River, N.J.

[73] Assignee: The Trustees of Columbia University in the City of New York, NY, N.Y.

[21] Appl. No.: 492,080

[22] PCT Filed: Mar. 28, 1995

[86] PCT No.: PCT/US95/03744

§ 371 Date: Jun. 28, 1995

§ 102(e) Date: Jun. 28, 1995

[87] PCT Pub. No.: WO95/26138

PCT Pub. Date: Oct. 5, 1995

Related U.S. Application Data

[63] Continuation-in-part of Ser. No. 218,666, Mar. 28, 1994, abandoned.

[51] Int. Cl.$^6$ .................................................. A61K 31/315
[52] U.S. Cl. ........................... 514/494; 514/635; 424/642
[58] Field of Search ........................... 424/642; 514/494, 514/635

[56] References Cited

U.S. PATENT DOCUMENTS

| | | |
|---|---|---|
| 3,960,745 | 6/1976 | Billany et al. |
| 4,587,266 | 5/1986 | Verdicchio |
| 4,853,978 | 8/1989 | Stockum |
| 5,031,245 | 7/1991 | Milner et al. |
| 5,089,205 | 2/1992 | Huang et al. |
| 5,133,090 | 7/1992 | Modak et al. |
| 5,164,107 | 11/1992 | Khan et al. |
| 5,208,031 | 5/1993 | Kelly ................................ 424/412 |
| 5,357,636 | 10/1994 | Dresdner, Jr. et al. |

FOREIGN PATENT DOCUMENTS

| | | |
|---|---|---|
| WO-93-18745 | 9/1993 | WIPO |
| WO-93-18852 | 9/1993 | WIPO |

OTHER PUBLICATIONS

Lawrence, J.C. et al., "Evaluation of Phenoxeotol—Chlorhexidine Cream as a Prophylactic Antibacterial Agent in Burns," The Lancet, pp. 1037–1040, May 8, 1992.

Fitzgerald, K.A., Davies, A., and Russel, A.D., "Mechanism of Action of Chlorhexidine Diacitate and Phenoxyethanol Singly and in Combination Against Gram–negative Bacteria," 215 Mibrobio 70:215–229 (1992).

Modak S. et al., "Rapid Inactivation of Infections Pathogess by Chlorhexidine Coated Gloves," Infection Control and Hospital Epidemiology, 13:463–471, (1992).

"Drug Information for the Health Care Professional," vol. 1A, USP–D1, 1989, Ninth Edition, pp. 792–793, Banta Company, VIR.

PDR—39th Edition, 1985, pp. 2037–2038, chlorhexidine.

PDR—39th Edition, 1985, p. 1858 Lotrisone.

Schmolka, I.R., "The Synergistic Effects of Nonionic Surfactants Upon Cationic Germicidal Agents," J. Soc. Cosmet. Chem., 24:577–592, 1973.

Goodman, Gillman's "The Pharmacological Basis of Therapeutics," A Textbook of Pharmacology, Toxicology, and Therapeutics for Physicians and Medical Students, Fourth Edition, p. 989 and Table of Contents, The Macmillan Co., 1970.

Heard, D.D., and Ashworth, R.W., "The Colloidal Properties of Chlorhexidine and its Interaction with Some Macromolecules," J. Pharm. Pharmac. 20:505–12, 1968.

Rubbo and Gardiner, "A Review of Sterilization and Disinfection, Year Book Medical Publishers," Chicago, 161–162 (1965).

Primary Examiner—William R. A. Jarvis
Attorney, Agent, or Firm—Brumbaugh, Graves, Donohue & Raymond

[57] ABSTRACT

A composition of matter containing zinc gluconate gel as an irritant-inactivating agent, and a substance which substantially prevents the irritant-inactivating agent from binding to the surface, wherein the irritant-inactivating agent in the composition is present in an amount effective to inactivate irritants in fluids which contact the composition, is described. Surgical instruments and physical barriers with the aforementioned composition applied thereto are also described. A method of inactivating irritants in a fluid contacting skin comprising applying the aforementioned composition to the skin is also disclosed. A method of inactivating irritants in a fluid contacting skin covered with a physical barrier comprising applying the aforementioned composition to the skin is also disclosed.

44 Claims, No Drawings

ZINC GLUCONATE GEL COMPOSITIONS

This application was filed pursuant to 35 U.S.C. §371 based on International Patent Application No. PCT/US95/03744, filed Mar. 28, 1995, and is a continuation-in-part of U.S. patent application Ser. No. 08/218,666, filed Mar. 28, 1994 now abandoned.

BACKGROUND OF THE INVENTION

The use of physical barriers such as gloves or condoms has been recommended to minimize the risk of contact with body fluids containing infectious microbial pathogens such as HIV (Human Immunodeficiency Virus) and hepatitis. However, it has been reported that a significant number of these physical barriers allow fluids to seep through existing or newly created pinholes. Furthermore, chemical or mechanical insults during use can damage glove surfaces, increasing permeability to viruses. Other than serving as a physical barrier, gloves do not provide any anti-microbial protection unless specifically coated with an anti-microbial agent. The development and manufacture of such coated gloves may be complicated and costly.

The common practice of washing hands with antiseptics prior to glove donning cannot provide adequate protection, because the necessary antiseptic concentration needed for rapid kill of subsequently intruding pathogens is not available from the residual amount of antiseptic left on a washed skin surface. Use of relatively large amounts of antiseptics such as HIBISTAT (0.5% chlorhexidine gluconate in 70% isopropanol) or HIBICLENS (4% chlorhexidine gluconate skin cleanser), while initially providing some protection, fails to fully inactivate intruding pathogens because of absorption of the anti-microbial agent to the skin. Existing barrier creams such as UNI SALVE (Smith and Nephew, Largo, Fla.) are also not effective for rapid inactivation.

U.S. Pat. No. 4,853,978 (Stockum) describes a glove having an inner coating containing an anti-microbial agent and cross-linked starch. However, such gloves release the anti-microbial agent slowly, and therefore cannot provide rapid disinfection. U.S. Pat. No. 5,089,205 (Huang et al.) describes processes for producing a glove having an internal anti-microbial surface. However, the glove resulting from such processes also fails to provide rapid disinfection.

U.S. Pat. No. 5,133,090 (Modak et al.) describes a glove having an inner coating comprising chlorhexidine which is capable of inactivating microbial pathogens such as HIV and HBV (Hepatitis B Virus). The glove described in U.S. Pat. No. 5,133,090 must be pretreated so as to prevent absorption of the chlorhexidine into the glove matrix. The glove described in U.S. Pat. No. 5,133,090 does not provide rapid microbial inactivation.

Glove use for protection from microbial pathogens is also known to give rise to allergic reactions in the skin of the glove wearer. Gloves, particularly latex gloves and gloves coated on the inside with starch powder, release allergens to which a wearer may be allergic.

Our invention provides, in part, a composition which can be used for rapidly inactivating microbial pathogens by application to a surface, such as skin. The anti-microbial agent in the composition does not bind to the surface due to the inclusion of an anti-binding substance in the composition, allowing the anti-microbial agent to be released in cidal doses when a fluid contacts the composition. In some embodiments, the anti-binding substance in the composition enhances the anti-microbial activity of the composition due to synergistic interaction with the anti-microbial agent.

Our composition overcomes some of the above-described problems associated with inactivation of microbial pathogens by providing the following advantages:

(1) when applied to skin, the anti-microbial agents in the composition minimally bind to the skin, permitting release of the anti-microbial agent and rapid microbial inactivation when the composition is contacted with a fluid;

(2) the composition may be applied to the hands prior to glove use, regardless of the type of glove used, thereby giving a glove-wearer more choice as to which type of glove to wear; and (3) anti-allergens in the composition minimally bind to the skin, allowing rapid inactivation of allergens released from gloves, thereby permitting a glove-wearer to wear a glove to which he might otherwise be allergic.

SUMMARY OF THE INVENTION

This invention provides a composition of matter for applying to a surface which comprises
  a) an irritant-inactivating agent, and
  b) a substance which substantially prevents the irritant-inactivating agent from binding to the surface,
wherein the irritant-inactivating agent in the composition is present in an amount effective to inactivate irritants in fluids which contact the composition.

This invention also provides a surgical instrument with the above-described composition applied thereto.

This invention also provides a physical barrier with the above-described composition applied thereto.

This invention further provides a method of inactivating irritants in a fluid contacting skin, which method comprises applying an effective irritant-inactivating amount of the above-described composition to the skin.

This invention further provides a method of inactivating irritants in a fluid contacting skin covered with a physical barrier, which method comprises applying an effective irritant-inactivating amount of the above-described composition to the skin.

This invention further provides a method of inactivating irritants in a fluid contacting skin, which method comprises applying to the skin an effective irritant-inactivating amount of a composition of matter comprising
  a) an irritant-inactivating agent; and
  b) a surfactant;
wherein the surfactant is present in an amount effective to substantially prevent the irritant-inactivating agent from binding to the skin and the amount of the irritant-inactivating agent is an amount effective to inactivate irritants in fluids which contact the composition.

Finally, this invention provides a method of inactivating irritants in a fluid contacting skin covered with a physical barrier, which method comprises applying to the skin an effective irritant-inactivating amount of a composition of matter comprising
  a) an irritant-inactivating agent; and
  b) a surfactant;
wherein the surfactant is present in an amount effective to substantially prevent the irritant-inactivating agent from binding to the skin and the amount of the irritant-inactivating agent is an amount effective to inactivate irritants in fluids which contact the composition.

DETAILED DESCRIPTION OF THE INVENTION

This invention provides a composition of matter for applying to a surface which comprises a) an irritant-inactivating agent, and b) a substance which substantially prevents the irritant-inactivating agent from binding to the surface, wherein the irritant-inactivating agent in the composition is present in an amount effective to inactivate irritants in fluids which contact the composition.

As used herein, the term "surface" is meant to include any surface. Examples of surfaces include, but are not limited to, countertops, surfaces of appliances, surfaces of surgical instruments, the surface of a wound dressing, the surface of a physical barrier such as a glove or a condom, and the surface of an animal, i.e. the animal's skin. The animal may be any animal, including a reptile, bird, or mammal. Accordingly, the above-described composition may be applied to any surface, including to the skin of a farm animal or a house-pet. The above-described composition may also be applied to the skin of a human.

The composition described above may be applied to the surface using any suitable application means. Suitable application means are known to those of ordinary skill in the art and include, but are not limited to, spraying the composition onto the surface, as well as spreading the composition onto the surface by hand.

The above-described composition comprises an irritant-inactivating agent in an amount effective to inactivate irritants in fluids which contact the composition. Accordingly, when the above-described composition is contacted with a fluid which contains irritants, the composition will inactivate the irritants. As used herein, the term "irritant" is meant to indicate any substance which causes an adverse reaction in an animal. Irritants include, but are not limited to, allergens and microbial pathogens such as viruses, bacteria, and fungi. The term "inactivate" is meant to indicate neutralizing the effects of the substance, for example by blocking the adverse reaction to the substance in the animal, as when an anti-allergen, such as an anti-histamine, blocks an animal's reaction to an allergen, or, if the irritant is a microbial pathogen, when an anti-microbial agent inhibits the growth of the pathogen, kills the pathogen, or causes the pathogen to lose its infectivity.

When the composition is contacted with a fluid which contains irritants, the composition may already have been applied to a surface. Accordingly, the composition may inactivate irritants in fluids which contact a surface to which the composition has already been applied.

The fluid which contains irritants may contain irritants which come into contact with the fluid after the fluid contacts a surface to which the composition has been applied. In such a case, the irritants may originate from the surface to which the composition has been applied, such as microbial pathogens already on the skin of an animal before the composition is applied to the animal's skin. Irritants already on the skin of an animal include microbial pathogens on the skin of an animal which was infected with the microbial pathogens before the composition was applied to the animal's skin. Alternatively, the irritants may originate externally to the surface, for example from the air surrounding the surface, and come into contact with the fluid already on the surface.

Furthermore, the fluid which contains irritants may contain irritants which come into contact with the fluid before the fluid contacts the surface to which the composition has been applied. An example of a fluid containing irritants which have come into contact with the fluid before the fluid contacts the surface is blood containing blood-borne pathogens, such as HIV, which contacts a surface to which the composition has been applied.

The above-described composition may also contact a fluid containing irritants when it is applied to a fluid-covered surface. Accordingly, the composition may inactivate irritants in fluids already present on a surface when the composition is applied to the surface.

The term "fluid" as used herein is meant to include any fluid. Accordingly, the above-described composition may inactivate irritants in a fluid originating from a surface to which the composition has been applied, such as perspiration originating from skin to which the composition has been applied. Alternatively, the composition may inactivate irritants in fluids originating externally to a surface to which the composition has been applied, such as biological fluids from another animal contacting the skin of an animal to which the composition has been applied. Examples of biological fluids are known to those skilled in the art and include, but are not limited to, blood, urine, feces, mucous, semen, saliva, serum, and perspiration. Likewise, when the above-described composition is applied to a fluid-covered surface, the fluid covering the surface may originate from the surface, or it may originate externally to the surface. Examples of such fluids include, but are not limited to, contaminated water and biological fluids such as those described above.

As used herein, the term "irritant-inactivating agent" is meant to indicate any substance which inactivates an irritant. Irritant-inactivating agents include, but are not limited to, anti-allergens, anti-microbial agents, or a combination thereof.

In one embodiment of the above-described composition, the irritant-inactivating agent is an anti-allergen or combination of anti-allergens. An "anti-allergen" is any substance which is capable of inactivating an allergen. Such substances are well known to those of ordinary skill in the art. Examples of anti-allergens include chlorpheniramine, diphenhydramine, carbinoxamine, pyrilamine, tripelennamine, brompheniramine, hydroxyzine, cyclizine, meclizine, promethazine, terfenadine, astemizole, dimenhydrinate, and pharmaceutically acceptable salts thereof. These and other examples of anti-allergens useful in this invention can be found in such references as *Goodman and Gilman's The Pharmacological Basis of Therapeutics* (Goodman Gilman, A., Rall, T. W., Nies, A. S., Taylor, P., 8th ed. (Pergamon Press; Elmsford, N.Y.: 1990)), the contents of which are hereby incorporated by reference.

In another embodiment, the irritant-inactivating agent is an anti-microbial agent or combination of anti-microbial agents. As used herein, the term "anti-microbial" agent means any substance which inactivates microbial pathogens. Anti-microbial agents include, but are not limited to, anti-viral, anti-bacterial, or anti-fungal substances. Anti-microbial agents also include substances possessing any combination of viricidal, bacteriocidal, or fungicidal properties. Anti-microbial agents are well known to those of ordinary skill in the art. Examples of anti-microbial agents include iodophors, iodine, benzoic acid, dehydroacetic acid, propionic acid, sorbic acid, methyl paraben, ethyl paraben, propyl paraben, butyl paraben, cetrimide, benzalkonium chloride, dequalinium chloride, chlorhexidine, chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, and pharmaceutically acceptable salts thereof. These and further examples of anti-microbial agents useful in this invention can be found in such references as *Goodman and Gilman's The Pharmacological Basis of Therapeutics*, supra.

If the irritant-inactivating agent in the above-described composition comprises an anti-microbial agent, the anti-microbial agent is preferably chlorhexidine or a pharmaceutically acceptable chlorhexidine salt. The pharmaceutically acceptable chlorhexidine salt may be any pharmaceutically acceptable chlorhexidine salt. Pharmaceutically acceptable chlorhexidine salts are well known to those of ordinary skill in the art and include, but are not limited to, chlorhexidine palmirate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulphate, chlorhexidine sulphite, chlorhexidine thiosulphate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate.

The above-described composition comprises a substance which substantially prevents the irritant-inactivating agent from binding to a surface (also referred to herein as "the anti-binding substance"). Accordingly, the irritant inactivating agent in the above-described composition does not substantially bind to a surface when the composition is applied to the surface. Without being limited by scientific theories, it is believed that irritant-inactivating agents bind to a surface by ionic interaction, although the anti-binding substance in the above-described composition can substantially prevent other types of binding of the irritant-inactivating agent to the surface. Binding of substances, including both ionic interactions and nonionic interactions, is well-known to those of ordinary skill in the art.

The anti-binding substance may work by combining with the irritant-inactivating agent. Accordingly, the anti-binding substance may comprise one or more substances which combine with the irritant-inactivating agent. As used herein, "combining with the irritant-inactivating agent" indicates any manner of engaging the irritant-inactivating agent so that the irritant-inactivating agent is prevented from binding to a surface.

For example, a substance may combine with an irritant-inactivating agent by statically adsorbing the irritant-inactivating agent. Accordingly, the substance which combines with the irritant-inactivating agent may comprise a substance or combination of substances which statically adsorb the irritant-inactivating agent. Substances capable of static adsorption are well-known to those of ordinary skill in the art and include, but are not limited to, relatively insoluble metal salts, such as zinc oxide, zinc carbonate, zinc oleate, zinc peroxide, zinc phosphate, zinc stearate, zinc undecylenate, zinc salicylate, titanium oxide, titanium dioxide, silver carbonate, silver iodate, silver iodide, silver oxide, silver sulfate, silver phosphate, silver sulfadiazine, silver palmirate, silver stearate, and silver oxalate.

A substance may also combine with an irritant-inactivating agent by providing interstitial spaces which entrap the irritant-inactivating agent within the substance. Accordingly, the substance which combines with the irritant-inactivating agent may comprise one or more substances comprising interstitial spaces which entrap the irritant inactivating agent. Substances comprising interstitial spaces are well-known to those of ordinary skill in the art and include, but are not limited to, relatively insoluble salts and polysaccharides, including mucopolysaccharides. Relatively insoluble salts include, but are not limited to, calcium carbonate, barium sulfate, aluminum silicate, calcium phosphate, calcium sulfate, barium carbonate, magnesium carbonate, and magnesium stearate. Polysaccharides include, but are not limited to, starch, methyl cellulose, ethyl cellulose, hydroxyethylcellulose, cationic hydroxyethylcellulose substituted with polyethyleneoxide (such as polyquaternium 10, manufactured by Amerchol Corporation), hydroxyethylcellulose substituted with a polyethyleneglycol alkylphenyl ether (such as nonoxynol hydroxyethylcellulose), dextran, dextran sulfate, and hyaluronic acid.

A substance may also combine with the irritant-inactivating agent by forming a matrix incorporating the irritant-inactivating agent. Accordingly, the substance which combines with the irritant-inactivating agent may comprise one or more substances which form a matrix. Examples of matrixes include, but are not limited to, gels. Substances capable of forming a gel are known to those of ordinary skill in the art, and include such substances as aluminum silicate, aluminum hydroxide, and aluminum chlorhydrate. As used herein, a substance which forms a matrix is any substance which will form a substantially continuous layer, such as a film, upon evaporation of a solvent in a solution containing the substance. When the irritant-inactivating agent is mixed in a solution with a substance which forms a matrix and the solvent of the solution is evaporated, the substance forms a matrix incorporating the irritant-inactivating agent. Substances which form a matrix are well known to those of ordinary skill in the art and include, but are not limited to, polymers and macromolecules such as silicone, teflon, polylactic acid, polyglycolic acid, polyurethane, polyethyleneoxide, cationic hydroxyethylcellulose substituted with polyethyleneoxide (such as polyquaternium 10), polyvinylpyrrolidone, polyoxyethylene ether, lanolin, and petrolatum.

Furthermore, the substance which substantially prevents an irritant-inactivating agent from binding to a surface may work by blocking binding sites on the surface. Accordingly, the anti-binding substance may comprise one or more substances which block binding sites on a surface to which the composition has been applied. As used herein, a substance which blocks binding sites on a surface is any substance which binds to sites on the surface to which the irritant-inactivating agent would otherwise bind, thereby blocking the binding sites and preventing the irritant-inactivating agent from binding to those sites.

For example, if the binding sites on the surface are anionic, the substance which blocks the binding sites on the surface may be a cationic substance. Anionic binding sites include skin proteins. Accordingly, a cationic substance may be used to block binding sites on skin.

Any pharmaceutically acceptable cationic substance may be used to block binding sites on the skin. Pharmaceutically acceptable cationic substances are well-known to those of ordinary skill in the art and include, but are not limited to, cations from relatively soluble zinc and silver salts, as well as quaternary ammonium compounds, including amphoteric quaternary ammonium compounds. Examples of relatively soluble zinc and silver salts include, but are not limited to zinc acetate, zinc gluconate, zinc sulfate, zinc undecylenate, zinc salicylate, silver acetate, silver lactate, silver nitrate, silver sulfadiazine, silver palmirate, silver stearate, and silver oxalate. Examples of quaternary ammonium compounds include, but are not limited to amino acids and peptides; substituted amino acids, such as cocodimonium hydroxypropyl silk amino acids, phenylthiohydantoin alanine, and phenylthiohydantioin glycine; proteins such as elastin, collagen, and keratin; quaternized proteins, such as cocodimonium hydroxypropyl hydrolyzed keratin, lauryldimonium hydroxypropyl hydrolyzed collagen, and stearyldimonium hydroxypropyl hydrolyzed collagen; and cationic hydroxyethylcellulose substituted with polyethyleneoxide, such as polyquaternium 10.

In a search to find the best possible metal salts to be used in combination with the irritant-inactivating agent, various zinc salts were evaluated. Surprisingly, one of the zinc salts i.e. zinc gluconate was determined to have a property of forming a gel matrix when mixed with water or alcohol, especially at high concentrations. When zinc gluconate was combined with chlorhexidine gluconate (CHG) the CHG became distributed in the gel matrix. This was especially so when the CHG solution was mixed with greater than 10% zinc gluconate solution. Other zinc salts mixed with CHG did not form a gel-matrix. This matrix, even when diluted with water or any water soluble cream base and applied to the hand, forms a protective film and provides a cooling and soothing effect. When skin to which this matrix is applied is exposed to fluids containing irritants, virtually instant inactivation of the irritants is noted. The binding of the irritant-inactivating agent to the hand surface is also substantially prevented.

It was also found that a gel matrix was formed when zinc gluconate was mixed with water or water and alcohol mixtures without any antimicrobial agents. This zinc gluconate gel-matrix in a water-soluble cream base can be used as a protective barrier film on skin or other surfaces. For example, it may be used to protect skin from irritants, such as allergens. It additionally provides a soothing effect to skin.

Accordingly, in one embodiment of the composition of the subject invention, the substance (b) comprises a metal salt of gluconate such as zinc gluconate. When the substance (b) comprises a metal salt of gluconate, the composition is in one embodiment in the form of a gel.

This invention thus further provides a gel for applying to a surface which comprises (a) chlorhexidine or a pharmaceutically acceptable chlorhexidine salt, such as chlorhexidine gluconate, and (b) zinc gluconate, wherein the chlorhexidine or pharmaceutically acceptable chlorhexidine salt in the composition is present in an amount effective to inactivate chlorhexidine-sensitive irritants in fluids which contact the composition.

As used herein, the term "chlorhexidine-sensitive irritants" means those irritants which are inactivated by chlorhexidine and pharmaceutically acceptable chlorhexidine salts. The terms "irritant" and "inactivate" are defined above.

By substantially preventing the irritant-inactivating agent from binding to the surface, the anti-binding substance imparts several advantageous qualities to the composition, including the ability to release the irritant-inactivating agent when contacted by a fluid, the possibility of containing a lower concentration of irritant-inactivating agent, and the ability to protect the surface from any harmful side-effects associated with absorption of the irritant-inactivating agent.

However, the amount of the anti-binding substance relative to the amount of the irritant-inactivating agent should not be so great as to prevent the irritant-inactivating agent from being released when a fluid contacts the composition.

Preferably, the ratio of the amount of the irritant-inactivating agent to the amount of the substance which substantially prevents the irritant-inactivating agent from binding to the surface in the composition is at least about 1:5, although some substances which substantially prevent the irritant-inactivating agent from binding to the surface permit even lower relative amounts of the irritant-inactivating agent, as will be described in further detail, infra. More preferably, the ratio of the amount of the irritant-inactivating agent to the amount of the substance which substantially prevents the irritant-inactivating agent from binding to the surface in the composition is from about 1:5 to about 2:1.

The irritant-inactivating agent in the above-described composition is present in an amount effective to inactivate irritants in fluids which contact the composition. Preferably, the amount of the irritant-inactivating agent present in the composition is an amount which is effective to inactivate irritants within about 2 minutes from the time the fluid contacts the composition. More preferably, the amount is effective to inactivate irritants within about 1 minute from the time the fluid contacts the composition.

An amount of the irritant-inactivating agent in the composition which is effective to inactivate irritants in fluids which contact the composition is that amount which will release an irritant-inactivating dose of the irritant-inactivating agent when the composition is contacted by a fluid. The amount of the irritant-inactivating agent will depend on various factors known to those of ordinary skill in the art. Such factors include, but are not limited to, the strength of the irritant-inactivating agent and the anticipated number of irritants in fluids which are anticipated to contact the composition. Determination of optimum amounts considering such factors is within the ordinary skill of those in the art and would not present undue experimentation. When the irritant-inactivating agent comprises an anti-allergen, and the anti-allergen is preferable present in the composition in an amount of from about 0.05% to about 5%. When the irritant-inactivating agent comprises an anti-microbial agent, the anti-microbial agent is preferably present in the composition in an amount of from about 0.5% to about 10%, even more-preferably in an amount of from about 0.5% to about 5%.

We have found that zinc and silver salts and anti-microbial agents are microbiocidally synergistic when combined together in a composition as described above. That is, a composition as described above, comprising an amount of a zinc or silver salt which by itself exhibits no microbiocidal properties, inactivates more microbial pathogens than a composition without the zinc or silver salt which is otherwise the same. Accordingly, when the irritant-inactivating agent in the above-described composition is an anti-microbial agent, and when the anti-binding substance comprises a zinc or silver salt, the amount of the irritant-inactivating agent relative to the amount of the anti-binding substance may be lower than when a zinc or silver salt is not used. When the irritant-inactivating agent is an anti-microbial agent, and when the anti-binding substance comprises a zinc or a silver metal salt, the ratio of the amount of the anti-microbial agent to the amount of the anti-binding substance is preferably from about 1:13 to about 2:1.

In one embodiment wherein the irritant-inactivating agent comprises an anti-microbial agent, the above-described composition may further comprises an anti-microbial synergist in addition to the anti-microbial agent and the substance which substantially prevents the anti-microbial agent from binding to the surface.

As used herein, the term "anti-microbial synergist" is meant to indicate a substance which in combination with an anti-microbial agent produces a microbiocidal effect greater than the added microbiocidal effects of the substance and the anti-microbial agent used separately. Anti-microbial synergists contemplated for use in the above-described composition include all anti-microbial synergists known to those of ordinary skill in the art. Known anti-microbial synergists useful in this invention may be found in such references as *Goodman and Gilman's, The Pharmacological Basis of Therapeutics*, supra. Examples of anti-microbial synergists which may be used with an anti-microbial agent when the anti-microbial agent is chlorhexidine or a pharmaceutically acceptable chlorhexidine salt include, but are not limited to, phenoxyethanol, phenylethyl alcohol, ethylene diamine tetraacetic acid, benzalkonium chloride, didecyldimethylammonium chloride, a polyethyleneoxide surfactant, interferon, lipase, protease, and glucosidase.

As used herein, the term "polyethyleneoxide surfactant" is meant to indicate any substance comprising ethylene oxide units, including substances comprising ethylene oxide units bound to a hydrophobe such as an alkylphenol, a fatty alcohol, a fatty acid, or sorbitol. Examples of polyethyleneoxide surfactants include, but are not limited to ethylene oxide/propylene oxide/butylene oxide block copolymers or heteropolymers, polyethyleneglycol nonylphenyl ethers (such as nonoxynol-9), polyethyleneglycol octylphenyl ethers, and sorbitan esters (such as polysorbate-80).

The terms "lipase" indicates any substance which will degrade lipids in the coating of a microbial pathogen. The term "protease" indicates any substance which will degrade proteins in the coating of a microbial pathogen. The term "glucosidase" includes any substance which will degrade polysaccharides in the coating of a microbial pathogen The above-described composition may be in any form suitable for application to a surface. Forms suitable for application to a surface are known to those of ordinary skill in the art. The form may be selected taking into account factors such as the chosen means for application of the composition to the surface. In one embodiment, the above-described composition is in an aqueous form. Aqueous forms include, but are not limited to, creams, lotions, gels, sprays, and film-forming bases. The term "film-forming base" indicates any aqueous form which will form a dry film after application to a surface, the film resulting, for example, from evaporation of solvents in the aqueous form. In another embodiment, the composition is in a non-aqueous form. Non-aqueous forms include, but are not limited to, powders and non-aqueous spray.

In another embodiment, the above-described composition further comprises an anti-inflammatory agent or combination of anti-inflammatory agents in addition to the irritant-inactivating agent and the substance which substantially prevents the irritant-inactivating agent from binding to the surface. As used herein, the term "anti-inflammatory agent" is meant to indicate any substance which will prevent or reduce inflammation in the skin of an animal. Such substances are well known to those of ordinary skill in the art. Examples of anti-inflammatory agents include, but are not limited to, cortisone, hydrocortisone, salicylic acid, mesalamine, methyl salicylic acid, betamethasone benzoate, betamethasone dipropionate, betamethasone valerate, dexamethasone, dexamethasone sodium phosphate, methylprednisolone acetate, triamcinoclone, triamcinoclone acetonide, alclometasone dipropionate, amcinonide, clobetasol propionate, clocortolone pivalate, desonide, desoximetasone, diflorasone diacetate, fluocinolone acetonide, fluocinonide, flurandrenolide, halcinonide, mometasone furoate, and pharmaceutically acceptable salts thereof. These and other anti-inflammatory agents useful in this invention may be found in such references as *Goodman and Gilman's The Pharmacological Basis of Therapeutics*, supra.

In another embodiment, the above-described composition further comprises a spermicide in addition to the irritant-inactivating substance and the anti-binding substance. The term "spermicide" is meant to indicate any substance which inactivates sperm. Spermicides which may be useful in this invention are well-known to those of ordinary skill in the art.

In formulating compositions of this invention it is contemplated that the formulations may further comprise ingredients which, while not having the activity of the above-named ingredients, will aid in the formulation and use of the composition as a whole. Examples of such ingredients are well-known to those of ordinary skill in the art of producing formulations for biological purposes. Examples of these ingredients include such substances as binders, emollients, preservatives (such as methyl paraben), lubricants, colorants, perfumes, and the like. Accordingly, when the surface contemplated is skin, the composition of this invention may contain ingredients which are added to known lotions or medicaments, which are physiologically acceptable to skin and which do not contain ingredients which will reverse or retard the action of the irritant-inactivating agent.

Alternatively, the composition may be added to pre-existing formulations provided that the ingredients in those formulations do not prevent or retard the activity of the claimed composition. In a preferred embodiment, the claimed composition can be added to creams and lotions which are commercially available. Examples of comercially available lotions include those lotions sold under the tradenames "SOFT-SENSE", "LOTION SOFT", AND "CUREL". SOFT-SENSE (Johnson & Son, Inc., Racine, Wis.) is known to contain purified water, glycerin USP, distearyldimonium chloride, petrolatum USP, isopropyl palmitate, 1-hexadecanol, tocopheryl acetate (vitamin E USP), dimethicone, titanium dioxide USP, methyl paraben, propyl paraben, sodium chloride, and fragrance. LOTION SOFT (Calgon Vestal, St. Louise, Mo.) is a nonionic moisturizing lotion which is known to contain mucopolysaccharide. CUREL (Bausch & Lomb Incorporated, Rochester, N.Y.) is known to contain deionized water, glycerin, quaternium-5, petrolatum, isopropyl palmitate, 1-hexadecanol, dimethicone, sodium chloride, fragrance, methyl paraben, and propyl paraben.

Accordingly, in one embodiment of the composition when the surface contemplated is skin, the composition may have the following formula:

2% chlorhexidine gluconate
2% zinc oxide
0.2% polyquaternium 10
0.3% methylparaben
0.5% phenoxyethanol
95% SOFT-SENSE.

In another embodiment when the surface contemplated is skin, the composition may have the following formula:

2% chlorhexidine gluconate
1% zinc oxide
0.2% polyquaternium 10

0.3% methylparaben
0.5% phenoxyethanol
96% LOTION SOFT.

In a further embodiment when the surface contemplated is skin, the composition may have the following formula:

2% chlorhexidine gluconate
2% zinc oxide
0.2% polyquaternium 10
0.3% methylparaben
0.5% phenoxyethanol
95% CUREL.

This invention also provides a surgical instrument with the above-described composition applied thereto. The anti-binding substance in the above-described composition substantially prevents the irritant-inactivating agent in the composition applied to the surgical instrument from binding to the surface of the surgical instrument. As used herein, the term "surgical instrument" is meant to indicate any instrument used in surgery or during the medical examination or treatment of a subject. Examples of surgical instruments include, but are not limited to, scalpels, catheters, scissors, forceps, and needles, as well as instruments used by dentists, such as dental picks and dental mirrors.

This invention also provides a physical barrier with the above described composition applied thereto. The anti-binding substance in the above-described composition substantially prevents the irritant-inactivating agent in the composition applied to the physical barrier from binding to the surface of the physical barrier. As used herein, the term "physical barrier" is meant to indicate any solid device which may be used to cover a surface.

In one embodiment, the above-described physical barrier is in the form of a wound dressing. In another embodiment, the above-described physical barrier comprises mammalian skin, natural rubber latex, polyvinyl chloride, silicone rubber, or polyurethane. When the physical barrier comprises mammalian skin, natural rubber latex, polyvinyl chloride, silicone rubber, or polyurethane, the physical barrier may be in the form of a glove or a condom.

This invention also provides a method of inactivating irritants in a fluid contacting skin, which method comprises applying an effective irritant-inactivating amount of the above-described composition to the skin.

In one embodiment, the aforementioned method inactivates irritants, including microbial pathogens and allergens, already on the skin before a fluid contacts the skin. Irritants already on skin include microbial pathogens on the skin of an animal which was infected with the microbial pathogens prior to the time the fluid contacts the animal's skin. When the fluid contacts the skin, the irritants on the skin come into contact with the fluid. The fluid which contacts the skin may originate from an external source, or it may originate from the skin itself, such as perspiration originating from the skin. In this embodiment, the composition may be applied to the skin either before or after the fluid contacts the skin.

In another embodiment, the aforementioned method inactivates irritants, including microbial pathogens and allergens, originating from an external source. Irritants originating from an external source include irritants borne in fluids, such as blood, which contact the skin. Examples of irritants borne in blood include HIV and hepatitis virus. In this embodiment, the composition may be applied to the skin either before or after the fluid contacts the skin.

This invention also provides a method of inactivating irritants in a fluid contacting skin covered with a physical barrier, which method comprises applying an effective irritant-inactivating amount of the above-described composition to the skin.

In one embodiment of the aforementioned method, the physical barrier is in the form of a wound dressing. In another embodiment, the physical barrier comprises mammalian skin, natural rubber latex, polyvinyl chloride, or polyurethane. When the physical barrier comprises mammalian skin, natural rubber latex, polyvinyl chloride, or polyurethane, it may be in the form of a glove or a condom.

The fluid which contacts the skin covered with the physical barrier may originate from an external source which penetrates the physical barrier, or it may originate from the skin itself, such as perspiration originating from the skin. The aforementioned method may inactivate irritants, including microbial pathogens and allergens, already on the skin before a fluid contacts the skin. Irritants already on skin include microbial pathogens on the skin of an animal which was infected with the microbial pathogens prior to the time the fluid contacts the animal's skin. When the fluid contacts the skin, the irritants on the skin come into contact with the fluid. The aforementioned method may also inactivate irritants, including microbial pathogens and allergens, originating from an external source. Irritants originating from an external source include irritants borne in fluids, such as blood, which penetrate the physical barrier and contact the skin. Examples of irritants borne in blood include HIV and hepatitis virus. Irritants originating from an external source also include allergens released from the physical barrier which contact the skin.

This invention also provides a method of inactivating irritants in a fluid contacting skin, which method comprises applying to the skin an effective irritant-inactivating amount of a composition of matter comprising a) an irritant-inactivating agent; and b) a surfactant;

wherein the surfactant is present in an amount effective to substantially prevent the irritant-inactivating agent from binding to the skin and the amount of the irritant-inactivating agent is an amount effective to inactivate irritants in fluids which contact the composition.

A surfactant may substantially prevents an irritant-inactivating agent from binding to the skin by complexing with the irritant inactivating agent. As used herein, the term "complexing with" is meant to indicate engaging the irritant-inactivating agent by hydrogen bonding or ionic interactions. Examples of ways in which a surfactant may "complex with" an irritant-inactivating agent include, but are not limited to, the surfactant forming micelles which adsorb the irritant-inactivating agent on their surface by hydrogen bonding or ionic interaction, or the surfactant forming micelles with the irritant-inactivating agent as a micellular component. Surfactants which complex with irritant-inactivating agents are known to those of ordinary skill in the art. Examples of surfactants which form complexes with irritant-inactivating agents and which may therefore be useful in this invention can be found in U.S. Pat. No. 5,164,107 (Khan et al.); U.S. Pat. No. 3,960,745 (Billany et al.); Heard, D. D., and Ashworth, R. W., *The Colloidal Properties of Chlorhexidine and its Interaction with Some Macromolecules* (J. Pharm. Pharmac., 20: 505–512, 1968); and Schmolka, I. R., *The Synergistic Effects of Nonionic Surfactants Upon Cationic Germicidal Agents* (J. Soc. Cosmet. Chem., 24: 577–592, 1971). The contents of the aforementioned patents and publications are hereby incorporated by reference.

In one embodiment of the aforementioned method, the irritant-inactivating agent is chlorhexidine, and the surfactant is a nonionic or anionic surfactant. When the irritant-inactivating agent is chlorhexidine, the surfactant is preferably a nonionic surfactant, such as a polyethyleneoxide surfactant.

By substantially preventing the irritant-inactivating agent from binding to the skin, the surfactant in the composition of the aforementioned method imparts several advantageous qualities to the composition, including the ability to release the irritant-inactivating agent when contacted by a fluid, the possibility of containing a lower concentration of irritant-inactivating agent in the composition, and the ability to protect the skin from any harmful side-effects associated with absorption of the irritant-inactivating agent. However, the amount of the surfactant relative to the amount of the irritant-inactivating agent should not be so great as to prevent the irritant-inactivating agent from being released from the composition when a fluid contacts the composition. Preferably, the ratio of the irritant-inactivating agent to the surfactant is from about 10:1 to about 5:1.

In one embodiment, the aforementioned method inactivates irritants, including microbial pathogens and allergens, already on the skin before a fluid contacts the skin. Irritants already on skin include microbial pathogens on the skin of an animal which was infected with the microbial pathogens prior to the time the fluid contacts the skin. When the fluid contacts the skin, the irritants on the skin come into contact with the fluid. The fluid which contacts the skin may originate from an external source, or it may originate from the skin itself, such as perspiration originating from the skin. In this embodiment, the composition may be applied to the skin either before or after the fluid contacts the skin.

In another embodiment, the aforementioned method inactivates irritants, including microbial pathogens and allergens, originating from an external source. Irritants originating from an external source include irritants borne in fluids, such as blood, which contact the skin. Examples of irritants borne in blood include HIV and hepatitis virus. In this embodiment, the composition may be applied to the skin either before or after the fluid contacts the skin.

Finally, this invention provides a method of inactivating irritants in a fluid contacting skin covered with a physical barrier, which method comprises applying to the skin an effective irritant-inactivating amount of a composition of matter comprising a) an irritant-inactivating agent; and b) a surfactant;

wherein the surfactant is present in an amount effective to substantially prevent the irritant-inactivating agent from binding to the skin and the amount of the irritant-inactivating agent is an amount effective to inactivate irritants in fluids which contact the composition.

In one embodiment of the aforementioned method, the irritant-inactivating agent is chlorhexidine, and the surfactant is a nonionic or anionic surfactant. When the irritant-inactivating agent is chlorhexidine, the surfactant is preferably a nonionic surfactant, such as a polyethyleneoxide surfactant.

By substantially preventing the irritant-inactivating agent from binding to the skin, the surfactant in the composition of the aforementioned method imparts several advantageous qualities to the composition, including the ability release the irritant-inactivating agent when contacted by a fluid, the possibility of containing a lower concentration of irritant-inactivating agent in the composition, and the ability to protect the skin from any harmful side-effects associated with absorption of the irritant-inactivating agent. However, the amount of the surfactant relative to the amount of the irritant-inactivating agent should not be so great as to prevent the irritant-inactivating agent from being released from the composition when a fluid contacts the composition. Preferably, the ratio of the irritant-inactivating agent to the surfactant is from about 10:1 to about 5:1.

In one embodiment of the aforementioned method, the physical barrier is in the form of a wound dressing. In another embodiment, the physical barrier comprises mammalian skin, natural rubber latex, polyvinyl chloride, or polyurethane. When the physical barrier comprises mammalian skin, natural rubber latex, polyvinyl chloride, or polyurethane, it may be in the form of a glove or a condom.

The fluid which contacts the skin covered with the physical barrier may originate from an external source which penetrates the physical barrier, or it may originate from the skin itself, such as perspiration originating from the skin. The aforementioned method may inactivate irritants, including microbial pathogens and allergens, already on the skin before a fluid contacts the skin. Irritants already on skin include microbial pathogens on the skin of an animal which was infected with the microbial pathogens prior to the time the fluid contacts the animal's skin. When the fluid contacts the skin, the irritants on the skin come into contact with the fluid. The aforementioned method may also inactivate irritants, including microbial pathogens and allergens, originating from an external source. Irritants originating from an external source include irritants borne in fluids, such as blood, which penetrate the physical barrier and contact the skin. Examples of irritants borne in blood include HIV and hepatitis virus. Irritants originating from an external source also include allergens released from the physical barrier which contact the skin.

This invention will be better understood from the Examples in the "Experimental Details" Section which follows. However, one skilled in the art will readily appreciate that the specific methods and results discussed merely illustrate, and are not intended, nor should they be construed, to limit the invention as described more fully in the claims which follow thereafter.

EXPERIMENTAL DETAILS

The abbreviation used in this Section are: CHX (chlorhexidine), CHG (chlorhexidine gluconate), CHA (chlorhexidine acetate), CHC (chlorhexidine hydrochloride), PXE (phenoxyethanol), HIV (Human Immunodeficiency Virus), HBV (Hepatitis B Virus), CFU (colony forming units), ATCC (American Type Culture Collection (Bethesda, Md.)), LTSB (lecithin-containing trypticase soy broth), HEC (hydroxyethylcellulose), and CPRM (chlorpheniramine maleate).

Mixtures for Preparing Compositions

EXAMPLE 1

A suspension of 12% cornstarch plus 4% CHG was prepared and allowed to slowly stir for 24 hours at 28°–30° C. The suspension was centrifuged, washed with water and dried at 100° C. for 2 hours.

EXAMPLE 2

A suspension of 12% cornstarch plus 4% CHA was prepared and allowed to slowly stir for 24 hours at 28°–30° C. The suspension was centrifuged, washed with water and dried at 100° C. for 2 hours.

EXAMPLE 3

A suspension of 12% zinc oxide plus 4% CHG was prepared and allowed to slowly stir for 24 hours at 28°–30°

C. The suspension was centrifuged, washed with water and dried at 100° C. for 2 hours.

EXAMPLE 4

A suspension of 12% zinc oxide plus 4% CHA was prepared and allowed to slowly stir for 24 hours at 28°–30° C. The suspension was centrifuged, washed with water and dried at 100° C. for 2 hours.

EXAMPLE 5

A suspension of 6% zinc oxide plus 6% cornstarch plus 4% CHG was prepared and allowed to slowly stir for 24 hours at 28°–30° C. The suspension was centrifuged, washed with water and dried at 100° C. for 2 hours.

Preparation of Compositions

EXAMPLES 6A–6E

The mixtures of Examples 1–5 were suspended in water at a concentration of 20%, providing Examples 6A–6E respectively.

EXAMPLE 7

A composition was prepared containing 7% of the mixture described in Example 1, 13% zinc oxide, and 80% water.

EXAMPLE 8

A composition was prepared containing 7% of the mixture described in Example 1, 13% zinc oxide, 1% phenoxyethanol, and 79% water.

EXAMPLE 9A–9E

Compositions were prepared containing 7% of the mixtures of Examples 1–5, 13% zinc oxide, 1% phenoxyethanol, 1% hydroxyethylcellulose, and 78% water, providing Examples 9A–9E, respectively.

EXAMPLE 10

The composition of Examples 6–9 may be prepared using any water-miscible cream, lotion, or film forming base which does not contain any CHX-inactivating compound in place of water.

Antimicrobial Evaluation Studies

Since the cidal concentration of CHG for HIV and HBV (1 minute kill) is the same as that for *Staphylococcus aureus*, we used *Staphylococcus aureus* as the test model for infectious pathogens.

EXAMPLE 11

In Vitro Efficacy of Compositions 0.1 mL of each composition tested was placed in each glove finger of a glove and spread all around. To each glove finger, 0.1 mL of blood containing $10^5$ CFU of *Staphylococcus aureus* (ATCC #10390)/mL was added and massaged for 2 minutes. 0.8 mL of CHX inactivating media (LTSB) was added to each glove finger, mixed, and 0.2 mL aliquots removed and subcultured on trypticase soy agar plates. After 24 hours, colony counts were measured. Results are shown in Table 1. These results demonstrate that compositions embodying the invention may inactivate microbial pathogens within 2 minutes upon fluid contact.

TABLE 1

Rapid Inactivation (2 minutes) of Pathogens by Compositions: In Vitro Method

| Composition | Bacterial Colonies (CFU/Finger) |
| --- | --- |
| Example 6A | 0 |
| Example 6B | 0 |
| Example 6C | 0 |
| Example 6D | 0 |
| Example 6E | 12 |
| Example 8 | 0 |
| Example 9A | 0 |
| 12.5% zinc oxide | 700 |
| Control (no composition) | 7640 |

EXAMPLE 12

Efficacy of Anti-microbial Compositions in Volunteers; Rapid Inactivation (2 minutes) of Pathogens by Compositions Example 12 was carried out to evaluate the protective effect of compositions representing different embodiments of the invention on hands prior to donning surgical gloves. After the volunteers applied the composition on their hands, gloves were donned for 3 hours before the test was carried out in order to simulate glove failure after an extended period of wearing and allow binding, if any, of the antimicrobial agent to the skin.

Procedure 2.8 ml of each composition tested was dispensed and spread uniformly on both hands and allowed to dry before donning gloves. Six volunteers took part in these studies. Each volunteer participated in the evaluation of test groups as well as control groups on different days. The volunteers disinfected their hands with 70% isopropanol before the experiment. Three volunteers applied one of three different compositions on their hands and donned the gloves for 3 hours. The other three volunteers donned the gloves without any formulation on their hands (control group) for 3 hours. This experiment was repeated on a daily basis by switching groups among the volunteers.

After 3 hours, 0.1 mL blood containing $10^5$ CFU of *Staphylococcus aureus*/mL was introduced into each glove finger. After 2 minutes, 0.9 mL LTSB was added, mixed, and 0.2 mL aliquots were removed and subcultured on trypticase soy agar plates and incubated at 37° C. After 24 hours, colony counts were determined. Results are shown in Table 2. The results in Table 2 demonstrate that composition embodying the invention retain the ability to rapidly inactivate microbial pathogens well-after they are applied to skin.

TABLE 2

Rapid Inactivation of Pathogens by Compositions: Volunteer Study

| Group | Bacterial Colonies MEAN CFU/FINGER (n = 10) |
| --- | --- |
| Example 7 | 35 |
| Example 6C | 0 |
| Example 8 | 0 |
| Example 9A | 0 |

TABLE 2-continued

Rapid Inactivation of Pathogens by Compositions: Volunteer Study

| Group | Bacterial Colonies MEAN CFU/FINGER (n = 10) |
| --- | --- |
| HIBISTAT* | 1302 |
| Control | 12,500 |

*Two volunteers dispensed 5 ml of HIBISTAT (as per the manufacturer's recommendation), spread it uniformly on both of their hands, and allowed it to dry. The gloves were then donned for 3 hours and challenged with bacteria as described above.

EXAMPLE 13

CHC-Zinc Oxide Composition

CHC was complexed with zinc oxide at a proportion of 1.2% CHC plus 13% zinc oxide. This composition was evaluated for its efficacy in rapidly inactivating pathogens using procedures as described in Example 12. Results are shown in Table 3. As is demonstrated by the results in Table 3, ZnO compositions embodying the invention rapidly inactivate microbial pathogens, even several hours after they have been applied to skin.

TABLE 3

Rapid Inactivation (2 minutes) of Pathogens by CHC-Zinc Composition in Human Volunteers

| Group | CFU/finger (average of 3 fingers) |
| --- | --- |
| 1.2% CHC in H$_2$O | 3190 |
| 1.2% CHC + 13% ZnO, (Example 13) | 15 |
| 12.5% ZnO | 700 |
| Example 8 | 0 |
| Control | 8900 |

EXAMPLE 14

Synergistic Activity of Zinc Oxide and CHX

CHG, ZnO, and a combination thereof was added to each glove finger. Glove fingers were then inoculated with 0.1 mL of blood containing $10^5$ CFU *Staphylococcus aureus*/mL. After 2 minutes, 0.9 mL of LTSB was added, and 0.2 mL of the extract were plated to determine colony counts. Results are shown in Table 4. The results in Table 4 demonstrate that ZnO compositions embodying the invention rapidly inactivate microbial pathogens.

TABLE 4

| Drug | CFU/glove finger |
| --- | --- |
| CHG [450 µG] | 1420 |
| ZnO [12.5 mg] | 1080 |
| CHG [450 µg] + ZnO [12.5 mg] | 230 |
| Control (no drug) | 8900 |

EXAMPLE 15

Synergistic Activity of Zinc Oxide and CHG, with Calcium Carbonate

Lotions were prepared using CHG complexed with calcium carbonate and were evaluated for their efficacy in rapidly inactivating pathogens as described in Example 11. Results are shown in Table 5. These results demonstrate that ZnO compositions embodying the invention rapidly inactivate microbial pathogens.

TABLE 5

Inactivation in 1 minute

| Lotion Composition | (CFU/Finger) |
| --- | --- |
| 6% calcium carbonate + 4% CHG + 2% zinc oxide | 30 |
| 6% calcium carbonate + 4% CHG | 170 |
| 5% zinc oxide | 1700 |
| Control (no composition) | 2420 |

EXAMPLE 16

Evaluation of the Synergistic Effect of Zinc Oxide on the Antimicrobial Efficacy of Chlorhexidine This experiment was carried out using the method described in Example 19, infra. CHG complexed with BRIJ 58 (polyoxyethylene ether) and HEC was tested with and without zinc oxide.

(1) 2% CHG+5% BRIJ 58+0.5% HEC+0.3% methylparaben+0.5% phenoxyethanol.

(2) 2% CHG+5% BRIJ 58+0.5% HEC+0.3% methylparaben+0.5% phenoxyethanol+2% ZnO.

(3) 2% ZnO+5% BRIJ 58+0.5% HEC+0.3% methylparaben+0.5% phenoxyethanol.

(4) Control (no composition).

Results are shown in Table 6. As is apparent from the results in Table 6, ZnO at this level shows no anti-microbial activity by itself (Group 3 in Table 6). However, when combined with CHG in a composition embodying this invention (Group 2 in Table 6), the ZnO increases the anti-microbial activity of an otherwise identical composition without the ZnO (Group 1 in Table 6). These results demonstrate the synergistic property of ZnO when used in compositions of this invention.

TABLE 6

| Group | Inactivation (1 minute Exposure) CFU/Finger |
| --- | --- |
| (1) | 114 |
| (2) | 29 |
| (3) | 1700 |
| (4) | 1700 |

EXAMPLE 17

Anti-allergenic Composition

A volunteer known to show an allergic reaction to CHX-coated natural rubber latex gloves participated in this study. 0.2 CPRM was added to the composition described in Example 8. The volunteer wore CHX-coated natural rubber latex gloves with an inner-starch layer ("CHX Glove"), and her reactions were noted. Her reaction to uncoated natural rubber latex gloves with an inner-starch layer ("Control Glove") was also noted. Results are shown in Table 7. The embodiment of this invention comprising the anti-allergen used in this experiment, prevented an allergic reaction to CHX-coated gloves in the subject. The subject also demonstrated a mild allergic reaction to the ordinary natural rubber latex gloves with the inner-starch layer, which the composition embodying the invention was also able to prevent. These results show that compositions embodying the invention, wherein the irritant-inactivating agent in the composition comprises an anti-allergen, will inactivate allergens released from a physical barrier covering skin to which the composition has been applied.

TABLE 7

Reaction to Composition/Glove Combinations

| Group | Allergic Reaction |
|---|---|
| Control Glove | Mild |
| CHX Glove | Positive |
| Example 8 + CPRM | None |
| Example 8 + CPRM and Control Glove | None |
| Example 8 + CPRM and CHX Glove | None |

EXAMPLE 18

Composition with Anti-microbial Synergist

This experiment was carried out using the method described in Example 14. Results are shown in Table 8. The results in Table 8 demonstrate that compositions embodying this invention, wherein the irritant-inactivating agent comprises an anti-microbial agent, may be combined with anti-microbial synergists to enhance the anti-microbial activity of the compositions.

TABLE 8

| Group | Bacterial Colonies (CFU/Finger) |
|---|---|
| 2 mg ZnO + 0.7 mg starch + 0.22 mg CHG | 3810 |
| 2 mg ZnO + 0.7 mg starch + 0.22 mg CHG + 0.15 mg phenoxyethanol | 345 |
| Control (no composition) | 9840 |

EXAMPLE 19

Effect of Addition of Certain Compounds on the Efficacy of Compositions (Inactivation in 1 Minute)

We have found the following procedure for evaluation of compositions containing CHX complexes to give almost identical results to those from the in vivo procedure described in Example 12. This following method obviates the need for volunteer studies, at least in preliminary experiments.

Procedure

Regular gloves were turned inside out (so as to allow the composition to be in contact with their inner surface) and then donned by volunteers who spread 2 mL of the test composition on both gloved hands. After drying, the gloves were left at room temperature for 1 hour. The gloves were then turned right side out and the three middle fingers were cut off at the palm. 10 µL of blood containing $10^5$ Staphylococcus aureus/mL was added to each finger and after 1 minute an aliquot was subcultured to determine colony counts.

Groups of compositions were tested. Results are given in Table 9 below. 0.3% methylparaben was used as a preservative in some of the groups. BRIJ 58 is a polymer (polyoxyethylene ether). These results show that zinc oxide and Phenoxyethanol potentiate the efficacy of CHX complexes, either synergistically or additively.

TABLE 9

| Group | Bacterial Counts (1 minute exposure) (CFU/Finger) |
|---|---|
| 2% zinc oxide + 2% CHG + 0.3% methylparaben | 20 |
| 2% zinc oxide + 2% CHG + 0.3% methylparaben + 0.2% phenoxyethanol | 0 |
| 0.5% phenoxyethanol | 682 |
| 2% zinc oxide + 2% CHG + 0.3% methylparaben + 5% BRIJ 58 | 10 |
| 2% zinc oxide + 2% CHG + 0.3% methylparaben + 5% BRIJ 58 + 0.2% phenoxyethanol | 0 |
| 2% CHG + 5% BRIJ 58 + 0.3% methylparaben | 177 |
| 2% CHG + 5% BRIJ 58 + 0.3% methylparaben + 0.2% phenoxyethanol | 140 |
| Control (no composition) | 1640 |

EXAMPLE 20

Binding of CHG to Hands by Compositions 2 mL of the following compositions were applied to both hands and gloves were donned on only one hand. Immediately after applying the composition, each ungloved finger was rinsed with 40 mL 0.01N HCl per finger and the CHG content of the HCl extract was determined (total CHG applied to the finger). After 30 minutes, each finger from the other hand was rinsed in 40 mL water, and the water extract was tested for CHG content (CHG unbound to the skin). The difference between the total CHG applied and the amount in the rinse water is taken as the amount bound to the hands. Results are given in Table 10. The results in Table 10 demonstrate that CHG in various embodiments of the invention does not substantially bind to skin.

TABLE 10

| | µg CHG/Finger | |
|---|---|---|
| Group | Total Applied | Bound (% Bound) |
| 4% CHG + 4% CaSO$_4$ + 2% ZnO | 2172 | 466 (22%) |
| 3% CHG + 4% CaCO$_3$ + 2% ZnO | 2310 | 458 (20%) |
| 3% CHG + 5% BRIJ 58 + 2% ZnO | 2245 | 553 (25%) |
| HIBISTAT | 1250 | 1000 (80%) |

EXAMPLE 21

Efficacy of Compositions as a Function of CHG Binding to the Skin

This efficacy test was carried out as in Example 19. The amount of CHG bound to the hand after 10 minutes was determined as described in Example 20. Results are shown in Table 11.

TABLE 11

| Composition | Bacterial Counts (1 minute Exposure) | |
| --- | --- | --- |
| | (µg/Finger) | (CFU/Finger) |
| 3% CHG + 4% CaCO₃ + 2% ZnO | 466 | 0 |
| 3% CHG + 5% BRIJ 58 + 2% ZnO | 553 | 0 |
| HIBISTAT | 1000 | 45 |
| Control (no formulation) | — | 1200 |

Example 21 was carried out to mimic condition where a composition is applied before donning examination gloves. We chose a 10 minute time period for testing the binding since this is the average time examination gloves are worn. The results in Table 11 show that CHG in HIBISTAT binds more to the skin, potentially increasing toxic side effects and greatly reducing its effectiveness. Furthermore, HIBISTAT contains alcohol and is irritating to the hand and cannot be used frequently (e.g. every 10 minutes in-between examinations). The results in Table 11 also show that the compositions embodying the invention possess superior anti-microbial activity to HIBISTAT.

The following additional experiments were carried out to evaluate agents which can be used along with CHG to prevent binding of the CHG to the skin. These agents do not interfere with the rapid release and action of the CHG.

EXAMPLE 22

Inactivation of Blood-Borne Pathogens by Compositions after 1 minute Exposure

Various slurries and creams were prepared containing CHG complexes, and their efficacy in rapidly (1 minute) inactivating pathogens in human volunteers was evaluated as in Example 12.

A) Slurry 1. 5% calcium carbonate+3% CHG+2% zinc oxide+5% Cetomacrogel non-ionic wax (BRIJ 58)+0.3% methylparaben.

B) Slurry 2. Same as Slurry 1, including 1% phenoxyethanol.

C) Cream 1. 4% calcium carbonate+4% CHG+2% zinc oxide in a water soluble cream base.

D) Cream 2. Same as Cream 1, including 1% phenoxyethanol.

E) Slurry 3. 5% calcium sulfate+3% CHG+2% zinc oxide+5% BRIJ 58+0.3% methylparaben.

F) Slurry 4. 5% BRIJ 58+3% CHG+2% zinc oxide+0.3% methylparaben.

G) Cream 3. 4% calcium sulfate+4% CHG+2% zinc oxide+5% BRIJ 58+0.3% methylparaben.

H) Cream 3A. Same as cream 3, but contains only 1% calcium sulfate.

I) Cream 4. Same as cream 3, including 1% phenoxyethanol.

J) Cream 5. 4% CHG+1% hyaluronic acid+1% calcium sulfate+1% elastin+2% zinc oxide+0.3% methylparaben+ 1% phenoxyethanol.

Results are shown in Table 12. These results demonstrate the anti-microbial activity of the embodiments described above.

TABLE 12

% Reduction of Pathogens when exposed for 1 minute to various compositions applied to volunteer's hands

| Group | CHG Bound/Finger µg CHG (Range) | Antimicrobial Efficacy % Reduction |
| --- | --- | --- |
| (A) Slurry 1 | 400–600 | 99–99.5 |
| (B) Slurry 2 | — | 100 |
| (C) Cream 1 | 500–700 | 99–99.5 |
| (D) Cream 2 | — | 100 |
| (E) Slurry 3 | 400–600 | 99–99.5 |
| (F) Slurry 4 | 400–600 | 99–100 |
| (G) Cream 3 | 500–700 | 99–99.5 |
| (H) Cream 3A | — | 99–99.5 |
| (I) Cream 4 | — | 100 |
| (J) Cream 5 | 500–700 | 100 |
| Control (no composition) | — | 0 |
| HIBISTAT (0.5% CHG) 12.5 mg/hand | 1,000–1,100 | 96.8 |

Inoculum = 10 µL 10⁵ CFU of _S. aureus_/mL of blood.

EXAMPLE 23

Anti-microbial Lotions

The following lotions were tested for binding of CHG to skin and for efficacy in inactivating pathogens:

1) 2% CHG+2% ZnO+0.2% polyquaternium-10+0.3% methyl paraben+0.5% phenoxyethanol+95% SOFT-SENSE.

2) 2% CHG+1% ZnO+0.2% polyquaternium-10+0.3% methyl paraben+0.5% phenoxyethanol+96% LOTION SOFT.

3) 2% CHG+2% ZnO+0.2% polyquaternium-10+0.3% methyl paraben+0.5% phenoxyethanol+95% CUREL.

The anti-microbial efficacy of each lotion was tested as in Example 12, with 2 mL of lotion applied to the hands, however gloves were donned for only 30 minutes prior to testing.

To test binding, 2 mL of lotion was applied to both hands and gloves were donned for 30 minutes. Gloves were removed, and both hands were washed with tap water. CHG which bound to the fingers was determined by soaking each finger in 40 mL of 0.01N HCl for 2 minutes. Note that in the binding tests, methyl paraben and phenoxyethanol were omitted from the lotions, since these substances interfere with the binding tests.

Results are given in Table 13. These results demonstrate that the CHG in the above lotions does not substantially bind to the hand, and that the above lotions are effective in inactivating microbial pathogens.

TABLE 13

| Lotion | µg CHG bound/finger | Inactivation of Pathogens (% Kill) |
| --- | --- | --- |
| 1 | 520 | 96–99 |
| 2 | 767 | 96–99 |
| 3 | 447 | 96–99 |

EXAMPLE 24

The following zinc salts were mixed with CHG for 1 hour and observed for the resulting product.

| GROUP (% of each ingredient) | PRODUCT |
| --- | --- |
| 1 (50% ZINC ACETATE + 20% CHG) | SUSPENSION |
| 2 (50% ZINC LACTATE + 20% CHG) | SUSPEESION |
| 3 (50% ZINC SULFATE + 20% CHG) | SUSPENSION |
| 4 (50% ZINC SALICYLATE + 20% CHG) | SUSPENSION |
| 5 (50% ZINC UNDECYLENATE + 20% CHG) | SUSPENSION |
| 6 (50% ZINC OXIDE + 20% CHG) | SUSPEESION |
| 7 (50% ZINC GLUCONATE + 20% CHG) | GEL |

The above products were diluted with water to a concentration of 10% zinc salt and 4% CHG and 2.0 mL was applied to the hand. Results are shown in Table 14, below.

TABLE 14

BINDING OF CHG IN FINGERS (μg CHG/finger)

| GROUP | μG/FINGER Range |
| --- | --- |
| 1 | 700–830 |
| 2 | 680–800 |
| 3 | 700–800 |
| 4 | 650–750 |
| 5 | 700–800 |
| 6 | 600–810 |
| 7 | 400–520 |
| 4% CHG in $H_2O$ | 1200–1500 |

EXAMPLE 25

Various zinc salts and CHG were mixed into the water miscible cream base described below. The zinc salt and CHG were first mixed for 1 hour in water at a concentration of 50% zinc salt+20% CHG and then diluted with water to a concentration of 24% zinc salt+8% CHG. This was further diluted with the cream base described below to yield 12% zinc salt+4% CHG. The final cream also contains 0.7% phenoxyethanol+0.3% methyl and ethyl parabens.

| CREAM BASE: Ingredients | Percentage (%) |
| --- | --- |
| Purified water | 78.5 |
| Cetyl alcohol | 5.0 |
| Trimethylammonium methosulfate | 3.5 |
| Methyl gluceth-20 | 3.0 |
| PPG-2 myristyl ether propionate | 3.0 |
| Mineral oil | 1.5 |
| Lanolin alcohol | 1.0 |
| Polyoxyethylerie(20) cetyl ether | 1.5 |
| 1-ethenyl-2-pyrrolidinone | 0.8 |
| Polyethylene oxide | 0.2 |

EXAMPLE 26

The following zinc salt and CHG combinations were prepared in the above cream base and tested for binding and antimicrobial efficacy.

BINDING STUDIES: 2.0 gms of the cream were applied to both hands and gloves were donned. After 30 minutes, the gloves were removed, hands washed for 1½ minutes with lukewarm water, and hands dried. The fingers of the hands were then dipped in 50 mL 0.01N HC for 2 minutes. The acid extract was used to measure the CHG levels.

| GROUP | μG CHG/FINGER |
| --- | --- |
| 12% Zn oxide + 4% CHG | 700–750 |
| 12% Zn gluconate + 4% CHG | 450–550 |
| 4% CHG in J & J Lotion (U.S. Pat. No. 4,587,266) | 1040–1200 |
| 4% CHG in Base | 900–1100 |

EXAMPLE 27

Rapid Inactivation Study—The creams were applied and the gloves donned as described in Example 26. After 30 minutes, 10 μL of blood containing Staph. aureus (CFU/mL) were introduced in each finger through a small cut and massaged. After 1 minute, 1.0 mL of CHG inactivating media was added to each finger, mixed, and aliquots removed and subcultured on trypticase soy agar plates. The colony counts were determined and the percent.

| GROUP | PERCENT KILL (%) |
| --- | --- |
| 12% Zn oxide + 4% CHG | 99 |
| 12% Zn gluconate + 4% CHG | 100 |
| 4% CHG in base | 90 |
| 4% CHG in J & J Lotion | 90 |
| Cream base | 10 |

DISCUSSION

We have described an anti-microbial composition which may be applied to human skin which will inactivate fluid-borne, including blood-borne, pathogens. The pathogens may be inactivated within 30 seconds to 1 minute after exposure to the fluid. This composition can be used alone or with a barrier system such as a glove or a condom. In one embodiment, a component of the composition complexes or combines with the anti-microbial agent. The aforementioned component comprises certain compounds or materials which prevent the anti-microbial agent in the composition from tightly binding to the skin, unlike other preparations, thus permitting the release of a cidal dose of the anti-microbial agent when the composition is exposed to fluids, including blood, containing fluid-born pathogens. Currently available preparations such as HIBISTAT (0.5% chlorhexidine gluconate in 70% isopropanol) or HIBICLENS (4% chlorhexidine gluconate skin cleanser) do not show rapid antimicrobial efficacy due to binding of the anti-microbial agent therein to the skin. Other preparations containing PCMX or quaternary ammonium compounds are not effective in the presence of blood.

We mixed chlorhexidine salts with starch, metal salts, polymers such as polyoxyethylene ethers, and hydrogels such as polyethyleneoxide and polyvinylpyrrolidone, in some cases forming micelles. We also combined chlorhexidine salts with zinc salts such as zinc oxide in synergistic proportions. Some compositions contained a number of the aforementioned components, and some contained phenoxyethanol. The compositions were formulated in suitable hydrophobic or hydrophilic vehicles, forming creams, lotions, gels, powders, suspensions, or film forming bases.

The compositions of the subject invention, for example, the zinc gluconate-CHG complex, can be used (1) as a vaginal cream to prevent sexually transmitted diseases, (2) on a wound dressing, (3) as a topical antimicrobial cream, (4) on medical devices and surgical instruments, (5) on a glove, or (6) on a condom. Other antimicrobials besides CHG such as parachlorometaxylenol (PCMX), triclosan (TC), povidone iodine (PVI), benzalkonium chloride (BZK), silver salts, polyoxyethylene alkylphenol (nonoxynol) compounds and anti-allergens can also be successfully incorporated into the zinc gluconate gel-matrix.

What is claimed is:

1. A composition comprising a gel matrix formed from zinc gluconate and a solvent selected from the group consisting of water, alcohol, and combinations thereof, wherein the zinc gluconate acts as the sole gelling agent.

2. The composition of claim 1, wherein the gel matrix comprises 50% zinc gluconate.

3. The composition of claim 1 which comprises at least 10% zinc gluconate.

4. The composition of claim 2 which comprises at least 10% zinc gluconate.

5. The composition of claim 1 wherein the gel matrix comprises a therapeutically effective amount of chlorhexidine or a pharmaceutically acceptable chlorhexidine salt.

6. The composition of claim 1 wherein the gel matrix comprises a therapeutically effective amount of an antimicrobial agent selected from the group consisting of parachlorometaxylenol, triclosan, povidone iodine, benzalkonium chloride, a silver salt, and a polyoxyethylene alkylphenol compound.

7. The composition of claim 1 wherein the gel matrix comprises a therapeutically effective amount of an anti-allergen.

8. The composition of claim 3 wherein the gel matrix comprises a therapeutically effective amount of chlorhexidine or a pharmaceutically acceptable chlorhexidine salt.

9. The composition of claim 3 wherein the gel matrix comprises a therapeutically effective amount of an antimicrobial agent selected from the group consisting of parachlorometaxylenol, triclosan, povidone iodine, benzalkonium chloride, a silver salt, and a polyoxyethylene alklylphenol compound.

10. The composition of claim 3 wherein the gel matrix comprises a therapeutically effective amount of an anti-allergen.

11. The composition of claim 4 wherein the gel matrix comprises a therapeutically effective amount of chlorhexidine or a pharmaceutically acceptable chlorhexidine salt.

12. The composition of claim 4 wherein the gel matrix comprises a therapeutically effective amount of an antimicrobial agent selected from the group consisting of parachlorometaxylenol, triclosan, povidone iodine, benzalkonium chloride, a silver salt, and a polyoxyethylene alkylphenol compound.

13. The composition of claim 4 wherein the gel matrix comprises a therapeutically effective amount of anti-allergen.

14. The composition of claim 5 which comprises between about 0.5% to 10% chlorhexidine or a pharmaceutically acceptable chlorhexidine salt.

15. The composition of claim 14 which comprises between about 0.5% to 5% chlorhexidine or a pharmaceutically acceptable chlorhexidine salt.

16. The composition of claim 8 which comprises between about 0.5% to 10% chlorhexidine or a pharmaceutically acceptable chlorhexidine salt.

17. The composition of claim 16 which comprises between about 0.5% to 5% chlorhexidine or a pharmaceutically acceptable chlorhexidine salt.

18. The composition of claim 11 which comprises between about 0.5% to 10% chlorhexidine or a pharmaceutically acceptable chlorhexidine salt.

19. The composition of claim 18 which comprises between about 0.5% to 5% chlorhexidine or a pharmaceutically acceptable chlorhexidine salt.

20. The composition of claim 1 which is a topical antimicrobial cream.

21. The composition of claim 5 which is a topical antimicrobial cream.

22. The composition of claim 6 which is a topical antimicrobial cream.

23. The composition of claim 7 which is a topical antimicrobial cream.

24. The composition of claim 1 which is a vaginal cream.

25. The composition of claim 5 which is a vaginal cream.

26. The composition of claim 6 which is a vaginal cream.

27. The composition of claim 7 which is a vaginal cream.

28. The composition of claim 1 which is applicable to a wound dressing.

29. The composition of claim 5 which is applicable to a wound dressing.

30. The composition of claim 6 which is applicable to a wound dressing.

31. The composition of claim 7 which is applicable to a wound dressing.

32. The composition of claim 1 which is applicable to a surgical instrument.

33. The composition of claim 5 which is applicable to a surgical instrument.

34. The composition of claim 6 which is applicable to a surgical instrument.

35. The composition of claim 7 which is applicable to a surgical instrument.

36. The composition of claim 1 which is applicable to a glove.

37. The composition of claim 5 which is applicable to a glove.

38. The composition of claim 6 which is applicable to a glove.

39. The composition of claim 7 which is applicable to a glove.

40. The composition of claim 1 which is applicable to a condom.

41. The composition of claim 5 which is applicable to a condom.

42. The composition of claim 6 which is applicable to a condom.

43. The composition of claim 7 which is applicable to a condom.

44. A method of preventing skin irritation comprising applying, to the skin, a composition comprising a gel matrix formed from zinc gluconate and a solvent selected from the group consisting of water, alcohol, and combinations thereof, wherein the zinc gluconate acts as the sole gelling agent.

* * * * *